United States Patent
Liu et al.

(10) Patent No.: US 10,793,701 B1
(45) Date of Patent: Oct. 6, 2020

(54) BASE COMPOSITION FOR MICRONEEDLE PATCH AND MICRONEEDLE PATCH COMPRISING THE SAME

(71) Applicant: WIN COAT CORPORATION, Hsinchu (TW)

(72) Inventors: Ta-Jo Liu, Hsinchu (TW); Hsiu-Feng Yeh, Hsinchu (TW); Yu-Sheng Lin, Hsinchu (TW); Yun-Hsuan Chen, Hsinchu (TW); Hung-Hsing Lin, Hsinchu (TW)

(73) Assignee: WIN COAT CORPORATION, Hsinchu (TW)

( * ) Notice: Subject to any disclaimer, the term of this patent is extended or adjusted under 35 U.S.C. 154(b) by 0 days.

(21) Appl. No.: 16/698,875

(22) Filed: Nov. 27, 2019

(30) Foreign Application Priority Data

Jul. 19, 2019 (TW) .............................. 108125602 A

(51) Int. Cl.

| | | |
|---|---|---|
| *C08L 1/28* | (2006.01) | |
| *C08L 29/14* | (2006.01) | |
| *A61M 37/00* | (2006.01) | |
| *C08L 39/06* | (2006.01) | |
| *B29L 31/00* | (2006.01) | |
| *B29C 41/04* | (2006.01) | |
| *B29C 39/42* | (2006.01) | |
| *B29K 31/00* | (2006.01) | |

(52) U.S. Cl.
CPC .......... *C08L 1/284* (2013.01); *A61M 37/0015* (2013.01); *C08L 29/14* (2013.01); *C08L 39/06* (2013.01); *A61M 2037/0023* (2013.01); *A61M 2037/0053* (2013.01); *B29C 39/42* (2013.01); *B29C 41/04* (2013.01); *B29K 2031/04* (2013.01); *B29K 2039/06* (2013.01); *B29K 2883/00* (2013.01); *B29L 2031/756* (2013.01); *B29L 2031/7544* (2013.01); *C08L 2203/02* (2013.01); *C08L 2205/025* (2013.01); *C08L 2205/03* (2013.01); *Y10T 428/1352* (2015.01)

(58) Field of Classification Search
CPC .......... C08L 1/284; C08L 29/14; C08L 39/06; C08L 2205/025; C08L 2203/02; C08L 2205/03; A61M 37/0015; A61M 2037/0023; A61M 2037/0053; B29L 2031/756; B29L 2031/7544; B29C 41/04; B29C 39/42; B29K 2883/00; B29K 2031/04; B29K 2039/06; Y10T 428/1352
See application file for complete search history.

(56) References Cited

FOREIGN PATENT DOCUMENTS

| CN | 102164576 A | 8/2011 |
|---|---|---|
| CN | 107412943 A | 12/2017 |
| CN | 109200012 A | 1/2019 |

*Primary Examiner* — James C Yager
(74) *Attorney, Agent, or Firm* — Pai Patent & Trademark Law Firm; Chao-Chang David Pai

(57) ABSTRACT

The present invention relates to a base composition for a microneedle patch and a microneedle patch comprising the same. The base composition comprises a first HPMC, a second HPMC and PVP/VA, wherein the viscosity of the first HPMC is greater than that of the second HPMC, the weight ratio of the first HPMC relative to the second HPMC is 1:0.1 to 1:1.2, and the amount of the PVP/VA is 0.25 wt % to 2 wt %. By controlling the constitution of the base composition, the microneedle patch can not only be demolded smoothly during the stage of the production, but also obtain the desired softness, flatness, flexibility, skin adhesion during the stage of use and humidity resistance during the stage of storage.

13 Claims, No Drawings

BASE COMPOSITION FOR MICRONEEDLE PATCH AND MICRONEEDLE PATCH COMPRISING THE SAME

CROSS-REFERENCE TO RELATED APPLICATION

Pursuant to 35 U.S.C. § 119(a), this application claims the benefits of the priority to Taiwan Patent Application No. 108125602, filed Jul. 19, 2019. The contents of the prior application are incorporated herein by its entirety.

BACKGROUND OF THE INVENTION

1. Field of the Invention

The present invention relates to a base composition and a microneedle patch, more particularly to a base composition and a microneedle patch applicable to cosmetic, medical, vaccine, and monitoring fields.

2. Description of the Prior Arts

Microneedle patches are painless injection systems that have been actively developed in recent years. Substrates of microneedle patches are covered with multiple micron-level microneedle structures. These microneedle structures can pierce the stratum corneum of skin and do not reach the nervous system below the epidermis, such that the active ingredients can be delivered and released to the epidermis without causing any pain. Administering active ingredients by using microneedle patches can not only solve numerous problems that have existed in oral administration or subcutaneous injection, but also is applicable to deliver both fat-soluble ingredients and water-soluble ingredients, so that the active ingredients of various types can be delivered to the epidermis directly and then released through microneedle structures of microneedle patches.

Conventional microneedle patches can be classified as solid microneedle patches, coated microneedle patches, hollow microneedle patches and dissolvable microneedle patches.

Solid microneedle patches are substantially fabricated from materials such as metal, ceramic or silicon, etc. Solid microneedle patches have sufficient mechanical strength; however, the broken microneedles remaining in the body may cause adverse effects. Therefore, the solid microneedle patches are currently less used. Coated microneedle patches, hollow microneedle patches, and dissolvable microneedle patches are mostly made from polymeric materials. Polyvinyl alcohol (PVA) is usually used as raw material for microneedles of the aforementioned various kinds of microneedle patches, which possesses both good film-forming property and mechanical strength; however, it has many problems in the processes of production, use and storage.

Specifically, in the drying and demolding steps of the preparation of microneedle patches, demolding cannot be smoothly performed if the degree of drying is not satisfactory. On the other hand, if drying is performed to a certain degree, the microneedles tend to be broken during demolding. This is attributed to the facts that the bases of the microneedles are hard and brittle after drying, which causes microneedle patches likely to break and lack skin adhesion when in use, and thus it is difficult to ensure every needle tip of microneedle patches pierce the stratum corneum of skin. In particular, PVA-made microneedle patches with over hygroscopicity further have several disadvantages such as difficulty in storage and short storage time, etc.

SUMMARY OF THE INVENTION

Based on the above, the objective of the present invention is to provide a more competitive microneedle patch to solve the aforementioned problems existing in the processes of production, use and storage of conventional microneedle patches.

To achieve the above-mentioned objective, the present invention provides a base composition for microneedle patches, which comprises a first hydroxypropyl methylcellulose (first HPMC), a second hydroxypropyl methylcellulose (second HPMC) and a polyvinylpyrrolidone/vinyl acetate copolymer (PVP/VA). The viscosity of the first HPMC is greater than that of the second HPMC. Based on a total weight of the overall base composition, the total amount of the first HPMC and the second HPMC is 0.1 percent by weight (wt %) to 3 wt %, the weight ratio of the first HPMC relative to the second HPMC is 1:0.1 to 1:1.2, and the amount of the PVP/VA is 0.25 wt % to 2 wt %.

By using an appropriate amount of the first HPMC, the second HPMC and PVP/VA in combination, a microneedle patch comprising a base which is made from the base composition has the following effects during the stages of production, use and storage:

(1) During the stage of production, the base of the microneedle patch can be dried to the required degree as desired and then demolded smoothly, and thus the breakage of base occurring during demolding can be avoided.

(2) During the stage of use, the base of the microneedle patch thereof not only can provide enough support to overcome the problem in the past that the base was likely to break, but also have properties of good softness, flatness, flexibility and skin adhesion, which ensure that every needle tip on the microneedle patch pierces the stratum corneum of skin.

(3) During the stage of storage, the base of the microneedle patch has low hygroscopicity, such that the problem of difficulty in storage can be overcome and the storage time thereof can be prolonged.

In accordance with the present invention, said first HPMC, second HPMC and PVP/VA are dissolvable or swellable materials; more specifically, these two HPMC and PVP/VA may be biocompatible materials or biodegradable materials.

In accordance with the present invention, the viscosities of said first HPMC and second HPMC are measured at 20° C. in 2% aqueous solution formulated by respectively dissolving either the first HPMC or second HPMC in water. This measurement condition is simply indicated as @20° C., 2% aqueous solution in the specification.

Preferably, the viscosity of the first HPMC measured at 20° C., 2% aqueous solution is 400 centipoise (cP) to 10,000 cP, more preferably 1,000 cP to 8,000 cP, still more preferably 1,500 cP to 6,000 cP, yet still more preferably 2,000 cP to 5,000 cP, and still further more preferably 3,000 cP to 4,500 cP. Preferably, the viscosity of the second HPMC measured at 20° C., 2% aqueous solution is 1 cP to 100 cP, more preferably 2 cP to 50 cP, still more preferably 2 cP to 30 cP, and yet still more preferably 3 cP to 20 cP.

Based on the total weight of the overall base composition, the total amount of the first HPMC and the second HPMC is preferably 0.2 wt % to 2.5 wt %, more preferably, the total amount of the first HPMC and the second HPMC is 0.2 wt % to 2 wt %, and still more preferably, the total amount of the first HPMC and the second HPMC is 0.5 wt % to 1.5 wt %.

Preferably, the weight ratio of the first HPMC relative to the second HPMC is 1:0.2 to 1:1.1, more preferably 1:0.2 to 1:0.8, and still more preferably 1:0.3 to 1:0.7.

Based on the total weight of the overall base composition, the amount of the PVP/VA is preferably 0.3 wt % to 2 wt %; and more preferably, the amount of the polyvinylpyrrolidone/vinyl acetate copolymer is 0.5 wt % to 2 wt %.

In accordance with the present invention, the base composition may be a mixture formed from dissolving the first HPMC, the second HPMC and PVP/VA in a solvent (e.g., water), which is also referred to as a base solution in the specification.

In one embodiment, the base solution consists of the first HPMC, the second HPMC, the PVP/VA and water.

Preferably, the solid content of the base composition is 0.35 wt % to 60 wt %, which indicates that the base composition contains 40 wt % to 99.65 wt % of water.

More preferably, the solid content of the base composition is 0.5 wt % to 30 wt %, still more preferably 1 wt % to 30 wt %, yet still more preferably 1.5 wt % to 30 wt %, and still further more preferably 1.75 wt % to 4 wt %. By controlling the solid content of the base composition, the unwanted void structures existing in the base of microneedle patches can be avoided; furthermore, the problems of extreme softness of the base for microneedle patch as well as deformation due to unbearable external force would be substantially overcome.

The viscosity of the base composition is measured at a shear rate of 1 $s^{-1}$ at 25° C. The viscosity of the base composition is preferably 1 cP to 200,000 cP, more preferably 1 cP to 100,000 cP, and still more preferably 100 cP to 500 cP.

Preferably, the pH of the base composition is in a range from 4 to 8, and more preferably, the pH of the base composition is in a range from 4 to 7.

Preferably, the surface tension of the base composition is less than or equal to 60 dyne/cm, more preferably, the surface tension of the base composition is more than or equal to 25 dyne/cm and less than or equal to 50 dyne/cm, and still more preferably, the surface tension of the base composition is more than or equal to 40 dyne/cm and less than or equal to 45 dyne/cm. When the surface tension of the base composition is too high, the defects such as unevenness, bubbles or concave/convex surfaces would exist in the base of the microneedle patch, resulting in that the produced microneedle patch has the structural imperfections in its base.

In accordance with the present invention, as the base composition of the present invention is chosen to produce a microneedle patch, the microneedle patch may be fabricated through, but are not limited to, the following methods. Specifically, the needle tip composition may be coated to or poured into a plurality of needle holes of a polydimethylsiloxane (PDMS) mold, and then vacuumed or centrifuged to remove the bubbles in the needle tip composition and fill the needle tip composition into the needle holes and spread evenly on the PDMS master mold. The thickness of a wet film is controlled by modifying the coating gap, coating thickness, or the volume of the needle tip composition, and the thickness of a dry film can be further controlled by modifying the condition of the drying step. After the needle tip of the microneedle patch is prepared, a middle layer, which can be designed based on various demands, as well as a base can be produced by the aforementioned methods and then a microneedle patch is accomplished.

Preferably, in the preparation of the microneedle patch, the base composition and/or the needle tip composition may be filled into the needle holes of the master mold by methods of, for example, but not limited to, blade or slot die coating, blade coating, slide coating, dip coating, inkjet printing or nozzle printing.

In the steps of removing bubbles and filling composition by vacuum, a degree of vacuum may be 0.001 torr to 90 torr. In another embodiment, in the steps of removing bubbles and filling composition by centrifugation, the rotational speed of centrifugation may be set at 100 revolutions per minute (rpm) to 10,000 rpm.

Preferably, in the preparation of the microneedle patch, the base composition can be dried by freeze drying or dried at room temperature to manufacture the base of the microneedle patch. Preferably, the temperature of the drying step may be controlled at −80° C. to 160° C., and the relative humidity of the drying step may be controlled at 40% to 75%. More preferably, the temperature of the drying step may be controlled at −20° C. to 100° C.

The present invention further provides a microneedle patch, which comprises multiple microneedle structures, each microneedle structure has a base and a needle tip formed thereon, and the base is made from the aforementioned base composition.

In the microneedle patch, the shape of each microneedle structure may be, but is not limited to, a conical shape, a pyramidal shape, or a steeple shape.

In the microneedle patch, the length of each microneedle structure may be smaller than 1,500 μm, more preferably smaller than 1,000 μm, and still more preferably 200 μm to 950 μm.

In the microneedle patch, the radius of the needle tip of each microneedle structure may be smaller than 15 μm, more preferably smaller than 11 μm, and still more preferably 5 μm to 10 μm. In addition, the tip angle of the needle tip of the microneedle patch may be less than 30°.

In the microneedle patch, the density of the microneedle structures may range from 100 needles/$cm^2$ to 1,000 needles/$cm^2$, and preferably range from 150 needles/$cm^2$ to 750 needles/$cm^2$.

Preferably, the mechanical strength of the microneedle patch may be larger than or equal to 0.045 N/needle, and more preferably, the mechanical strength of the microneedle patch may be larger than or equal to 0.058 N/needle.

Other objectives, advantages and novel features of the invention will become more apparent from the following detailed description when taken in conjunction with the accompanying drawings.

DETAILED DESCRIPTION OF THE PREFERRED EMBODIMENTS

Several base compositions for fabricating a microneedle patch are exemplified below to illustrate the implementation of the present invention. One person skilled in the art can easily realize the advantages and effects of the present invention in accordance with the contents disclosed in the specification. Various modifications and variations could be made in order to practice or apply the present invention without departing from the spirit and scope of the invention.

Description of Reagents

1. First hydroxypropyl methylcellulose (first HPMC):
   (1) 65SH-400, viscosity: 400 cP, purchased from Shin-Etsu Chemical Co., Ltd.;

(2) 65SH-1500, viscosity: 1,500 cP (@20° C., 2% aqueous solution), purchased from Shin-Etsu Chemical Co., Ltd.;
(3) 90SH-4000, viscosity: 4,000 cP (@20° C., 2% aqueous solution), purchased from Shin-Etsu Chemical Co., Ltd.;
(4) 90SH-4000SR, viscosity: 4,000 cP (@20° C., 2% aqueous solution), purchased from Shin-Etsu Chemical Co., Ltd.;
(5) 65SH-4000, viscosity: 4,000 cP (@20° C., 2% aqueous solution), purchased from Shin-Etsu Chemical Co., Ltd.;
(6) 60SH-4000, viscosity: 4,000 cP (@20° C., 2% aqueous solution), purchased from Shin-Etsu Chemical Co., Ltd.;
(7) 60SH-10000, viscosity: 10,000 cP (@20° C., 2% aqueous solution), purchased from Shin-Etsu Chemical Co., Ltd.
2. Second hydroxypropyl methylcellulose (Second HPMC):
   (1) PHARMACOAT 603, viscosity: 3 cP (@20° C., 2% aqueous solution), purchased from Shin-Etsu Chemical Co., Ltd.;
   (2) SB-4, viscosity: 4 cP (@20° C., 2% aqueous solution), purchased from Shin-Etsu Chemical Co., Ltd.;
   (3) PHARMACOAT 645, viscosity: 4.5 cP (@20° C., 2% aqueous solution), purchased from Shin-Etsu Chemical Co., Ltd.;
   (4) PHARMACOAT 606, viscosity: 6 cP (@20° C., 2% aqueous solution), purchased from Shin-Etsu Chemical Co., Ltd.;
   (5) PHARMACOAT 615, viscosity: 15 cP (@20° C., 2% aqueous solution), purchased from Shin-Etsu Chemical Co., Ltd.;
   (6) METOLOSE 65SH-50, viscosity: 50 cP (@20° C., 2% aqueous solution), purchased from Shin-Etsu Chemical Co., Ltd.;
   (7) METOLOSE 60SH-50, viscosity: 50 cP (@20° C., 2% aqueous solution), purchased from Shin-Etsu Chemical Co., Ltd.
3. Polyvinyl alcohol, purchased from Nippon Synthetic Chemical Industry Co., Ltd.
4. Polyvinylpyrrolidone/vinyl acetate copolymer, product name: Kollidon®, purchased from BASF Corporation.
5. Trehalose, product name: TREHA®, purchased from Hayashibara Co., Ltd.
6. Carboxymethyl cellulose (CMC), purchased from Sigma-Aldrich.
7. β-cyclodextrin (β-CD), product name: β-cyclodextrin, purchased from Yiyang Industrial Co., Ltd.

Preparation of Base Solution

Base solution of Examples and Comparative Examples were each obtained by mixing the aforementioned reagents according to the constitution shown in the following Table 1 with water.

TABLE 1

The constitution of the base solution of Examples (E1 to E4) and Comparative Examples (C1 to C9).

| | First Component | | Second Component | | Third Component | |
|---|---|---|---|---|---|---|
| | Type | Amount | Type | Amount | Type | Amount |
| E1 | First HPMC | 1 wt % | Second HPMC | 0.25 wt % | PVP/VA | 2 wt % |
| E2 | First HPMC | 1 wt % | Second HPMC | 0.5 wt % | PVP/VA | 1 wt % |
| E3 | First HPMC | 1 wt % | Second HPMC | 0.5 wt % | PVP/VA | 0.5 wt % |
| E4 | First HPMC | 1 wt % | Second HPMC | 0.5 wt % | PVP/VA | 0.25 wt % |
| C1 | PVA | 16.8 wt % | TREHA | 16.8 wt % | β-CD | 8.4 wt % |
| C2 | Second HPMC | 2 wt % | TREHA | 4 wt % | — | — |
| C3 | PVP/VA | 8 wt % | TREHA | 2 wt % | — | — |
| C4 | Second HPMC | 1 wt % | CMC | 9 wt % | — | — |
| C5 | PVP/VA | 8 wt % | CMC | 2 wt % | — | — |
| C6 | Second HPMC | 2 wt % | β-CD | 3 wt % | — | — |
| C7 | First HPMC | 2 wt % | PVP/VA | 1 wt % | — | — |
| C8 | First HPMC | 1 wt % | Second HPMC | 1 wt % | — | — |
| C9 | First HPMC | 1 wt % | Second HPMC | 0.5 wt % | PVP/VA | 4 wt % |

In the above table, the first HPMC and second HPMC of Examples 1 to 4 may be any of the reagents exemplified above. Specifically, the first HPMC may be 60SH-4000, and the second HPMC may be PHARMACOAT 645; the viscosity of the selected first HPMC is greater than that of the selected second HPMC, regardless of the combination of the first HPMC and second HPMC. By contrast, the first HPMC in Comparative Examples 7 to 9 may also be any of the reagents exemplified above. Specifically, the first HPMC is 60SH-4000. The second HPMC in Comparative Examples 2, 4, and 7-9 may also be any of the reagents exemplified above. Specifically, the second HPMC is PHARMACOAT 645.

The solid content, viscosity and surface tension of the base solution in each of Examples and Comparative Examples are shown in Table 2 below. The viscosity of each of the base solutions is measured by using a viscometer (instrument model: MCR302, purchased from Anton Paar) at 25° C. with a shear rate of 1 $s^{-1}$. The surface tension of each of the base solutions is measured at 25° C. by using FACE Automatic Surface Tensiometer (instrument model: CBVP-A3) through the wilhelmy plate method.

The viscosity of the base solution of Comparative Example 1 was too high, so the surface tension thereof could not be measured. In addition, precipitated crystals were observed in the base solution of Comparative Example 6 through the naked eye, so the viscosity and the surface tension thereof were not further measured, either.

Preparation of Microneedle Patch

In the production process, a microneedle patch was made from the base solution of each of Examples and Comparative Examples mentioned above through the method described below.

First of all, many needle holes of the PDMS master mold were coated by using the blade or slot die coating with the coating gap of 1,000 μm and at the coating speed of 3 m/min. The needle tip solution was 20 wt % aqueous solution of copper peptide and poly(methyl vinyl ether-alt-maleic anhydride), i.e., the needle tip solution contained 80 wt % of water as well as 20 wt % of mixture of copper peptide and poly(methyl vinyl ether-alt-maleic anhydride). The viscosity of the needle tip solution measured at a shear rate of 1 $s^{-1}$ at 25° C. was 40 cP, and the surface tension thereof was 30 dyne/cm. Next, the PDMS master mold coated with the needle tip solution was placed in a vacuum oven at a pressure of 20 torr and evacuated, so that the needle tip solution was filled into the needle holes of the master mold. The density of the needle holes on the master mold was 289 holes/cm$^2$; the array of the holes was 1.5 cm×1.5 cm; the shape of the holes was pyramidal; the depth thereof was about 600 μm; and the maximum width thereof was about 300 μm. Then, the solution of the needle tip composition was dried at 30° C. and under the relative humidity of 30% to 50% for 1 hour, thereby making the needle tip solution dry and form into needle tips.

Afterwards, the base solutions in the aforementioned Examples and Comparative Examples were respectively chosen to fill into many needle holes of the PDMS master mold using the blade or slot die coating with the coating gap of 1,600 μm and at the coating speed of 3 m/min. Next, the PDMS master mold coated with the base solution was placed in a vacuum oven at a pressure of 35 torr and evacuated, so that the base solution was filled into the needle holes of the master mold. Then, the base solution was dried at 30° C. and the relative humidity of 45% to 75% for 1 hour, thereby making the base solution dry and form into the base with the water amount less than 20%. Then, the microneedle structure with a base and a needle tip formed on the base can be demolded from the PDMS master mold, and the production of the microneedle patch was completed.

The microneedle patches of Examples and Comparative Examples were respectively subjected a compressive test with the displacement set to 10 mm, the speed set to 66 mm/min, and 500 compressive stress values received per second at the same time by using a universal material testing machine (instrument model 3343, purchased from INSTRON) to measure the mechanical strengths of the microneedle patches.

In the preparation of the microneedle patch by using the base solution of Comparative Example 4, deformation of the microneedle patch occurred during demolding, so the mechanical strength of the microneedle patch could not be further measured. In the preparation of the microneedle patch by using the base solution of Comparative Example 5, the microneedle patch was broken because of its brittle base during demolding, so the mechanical strength thereof could not be further measured, either. Therefore, only the mechanical strengths of the microneedle patches produced by using the base solution of Examples 1 to 4, Comparative Examples 1 to 3 and Comparative Examples 6 to 9 were listed in Table 2 below.

TABLE 2

The properties of the base solution of Examples and Comparative Examples and the mechanical strength of the microneedle patches produced therefrom.

| | Base Solution | | | Microneedle Patch Mechanical |
|---|---|---|---|---|
| | Solid Content (wt %) | Viscosity (cP) | Surface Tension (dyne/cm) | Strength (N/needle) |
| E1 | 3.25 | 235.8 | 43.6 | 0.15 |
| E2 | 2.5 | 230.7 | 43.9 | 0.14 |
| E3 | 2 | 242.3 | 43.8 | 0.13 |
| E4 | 1.75 | 199.2 | 43.4 | 0.13 |
| C1 | 42 | 250000 | — | 0.014 |
| C2 | 6 | 7.2 | 44.2 | 0.065 |
| C3 | 10 | 2.4 | 43.8 | 0.25 |
| C4 | 10 | 3803.9 | 43.9 | — |
| C5 | 10 | 27.5 | 44.1 | — |
| C6 | 5 | — | — | 0.003 |
| C7 | 3 | 125.7 | 44.5 | 0.17 |
| C8 | 2 | 241.2 | 43.9 | 0.1 |
| C9 | 5.5 | 257.3 | 43.4 | 0.16 |

Test Example 1: Demolding Evaluation

This test example aimed to observe the situation that the microneedle structures each having a base and a needle tip formed thereon were demolded from the PDMS master mold. In the stage of producing a microneedle patch, if the microneedle structure could be smoothly demolded from the PDMS master mold without damaging the structure of the base, mark "◦" in Table 3 below. If the microneedle structure could not be demolded from the PDMS master mold smoothly or the base was brittle and broken or damaged during demolding, mark "x" in Table 3 below.

Test Example 2: Properties Evaluation of a Microneedle Patch

In this test example, the softness and skin adhesion of each microneedle patch were evaluated by 5 people with visual observation and the actual experience after completion of the production of a microneedle patch, and the observation and sensory responses from these people were also listed in Table 3 below.

In addition, in the evaluation of the flatness of a microneedle patch, after cutting off the excess edge material from the demolded microneedle patch, the demolded microneedle patch was laid flat on a flat marble platform and then shot with a camera that was laid flat on the platform to observe whether the microneedle patch was flat on the marble platform. If a microneedle patch was flat on the marble platform and the microneedle structure was not observed to be warped or partially warped, the flatness of the microneedle patch was determined to be good and then marked "◦" in Table 3 below. On the contrary, if a microneedle patch was observed that it was unable to be flat on the marble platform and was warped or partially warped, the flatness of the microneedle patch was determined to be poor and then marked "x" in Table 3 below.

Further, in the evaluation of the flexibility of a microneedle patch, the microneedle patch was bent into a radius of curvature of 7.5 mm and was observed whether it was broken or deformed. If the microneedle patch was not broken or deformed after bending, the flexibility of the microneedle patch was determined to be good and then marked "◦" in Table 3 below. On the contrary, if the microneedle patch was broken or deformed after bending, the flexibility of the microneedle patch was determined to be poor and then marked "x" in Table 3 below.

The humidity resistance described in Table 3 below was evaluated whether the microneedle patch maintained 90% of the original mechanical strength after being placed in an environment of the ambient temperature of 25° C. and the relative humidity of 60% for 5 days. The mechanical strength was measured as described above. If the microneedle patch maintained 90% of the original mechanical strength after being placed in the aforementioned environment for 5 days, it was indicated that the humidity resistance of the microneedle patch was good and marked "○" in Table 3 below. On the contrary, if the mechanical strength of the microneedle patch was below 90% of the original mechanical strength after being placed in the aforementioned environment for 5 days, it was indicated that humidity resistance of the microneedle patch was poor and marked "x" in Table 3 below.

TABLE 3

The results of the microneedle patches prepared by base solutions of Examples 1 to 4 and Comparative Examples 1 to 9 at the stages of production, use and storage

| | Stage of Production | Stage of Use | | | | Stage of Storage |
|---|---|---|---|---|---|---|
| | Demolding Evaluation | Softness | Flatness | Flexibility | Skin adhesion | Humidity Resistance |
| E1 | ○ | ○ | ○ | ○ | ○ | ○ |
| E2 | ○ | ○ | ○ | ○ | ○ | ○ |
| E3 | ○ | ○ | ○ | ○ | ○ | ○ |
| E4 | ○ | ○ | ○ | ○ | ○ | ○ |
| C1 | x | x | x | ○ | ○ | x |
| C2 | ○ | ○ | ○ | ○ | ○ | x |
| C3 | x | x | x | ○ | ○ | x |
| C4 | x | x | x | x | x | ○ |
| C5 | x | x | x | x | x | ○ |
| C6 | ○ | x | x | ○ | ○ | ○ |
| C7 | ○ | x | x | ○ | ○ | x |
| C8 | ○ | x | x | ○ | ○ | ○ |
| C9 | ○ | x | ○ | x | x | ○ |

Since the stability of the base solution of Comparative Example 1 was relatively poor, the problem of surface drying and unevenness was liable to occur, which resulted in difficult demolding. In addition, by using the base solution of Comparative Example 1, the hygroscopicity of the base of the microneedle patch was relatively high, resulting in failure to store the microneedle patch for a long time and adversity for use in the industry. Further, for Comparative Example 1, the base of the microneedle patch was not as soft as expected and the flatness was insufficient, so the microneedle patch manufactured therefrom was still unfavorable for use.

Regarding the experimental results corresponding to Comparative Example 2 and Comparative Example 3, even if PVA was replaced by either HPMC or PVP/VA, the hygroscopicities of the bases of the microneedle patches were not effectively improved, which also resulted in failure to store these microneedle patches for a long time. In addition, for Comparative Example 3, an external force was further required during the demolding process, and the structure of the base of the microneedle patch was too soft and easily deformed, which resulted in poor softness and flatness of the microneedle patch.

Regarding Comparative Example 4 and Comparative Example 5, if HPMC or PVP/VA was used in combination with CMC, the problem of too high hygroscopicity could be overcome by using the base solutions of Comparative Example 4 and Comparative Example 5. However, the film-forming property of the base solution of Comparative Example 4 was poor. The base prepared by using the base solutions of Comparative Example 4 and Comparative Example 5 cannot be demolded without an external pulling force, unfortunately, the microneedle patch of Comparative Example 4 was deformed during the demolding process, and the microneedle patch of Comparative Example 5 was even broken during the pulling process. These problems severely degraded the qualities of the microneedle patches. In addition, as the bases of the microneedle patches manufactured by using the base solution of Comparative Example 4 and Comparative Example 5 were both too hard, the softness, flatness, flexibility and skin adhesion of the microneedle patches of Comparative Example 4 and Comparative Example 5 did not qualify for use.

Similarly, even if the problem of too high hygroscopicity could be overcome by using the base solution of Comparative Example 6 formulated by combining a single HPMC and β-CD, the problems of hard structures and brittleness also existed in Comparative Example 6 as described in Comparative Example 5, which resulted in poor softness. Further, crystals were precipitated in the base solution of Comparative Example 6, which further resulted in that the microneedle patch manufactured therefrom has defects of structural unevenness.

In addition, if a single HPMC and PVP/VA were combined to formulate the base solution of Comparative Example 7, the base manufactured therefrom could be demolded smoothly in the production process. However, problems of warped structures and extremely soft base were liable to occur due to compression. On the other hand, if only two HPMCs with different viscosities were combined and formulated into the base solution of Comparative Example 8, as described in Comparative Example 7, problems of warped structures and soft microneedles were liable to occur due to compression. Accordingly, regardless of the base solution of Comparative Example 7 or that in Comparative Example 8, the microneedles manufactured therefrom both failed to obtain the desired softness and flatness. In particular, the microneedle patch manufactured by using the base solution of Comparative Example 7 had the problem of too high hygroscopicity and could not be stored for a long time.

Further, if PVP/VA was further added to the combination of two HPMCs with different viscosities to formulate the solution of the base composition in Comparative Example 9, the base manufactured therefrom was hard because of too high content of PVP/VA, which resulted in problems of failing to withstand external forces and being prone to breaking. Therefore, even if two HPMCs and PVP/VA were mixed to formulate the base solution, the softness, flexibility and skin adhesion of the microneedle patch could not be improved.

In contrast with Example 1 to Example 4, the base solutions were formulated by combining appropriate amount of the first HPMC, the second HPMC, and the PVP/VA, the base of microneedle patch could withstand external forces without being brittle and broken, and the microneedle patch manufactured therefrom could maintain high mechanical strength. Moreover, the base of the microneedle patch of each of Example 1 to Example 4 could also have good softness, flatness, flexibility and skin adhesion, as well as good humidity resistance.

Based on the above test results, by using appropriate amount of the first HPMC, the second HPMC and PVP/VA in combination, the microneedle patch can be demolded smoothly during preparation, and the base of the microneedle patch can have desired softness, flatness, flexibility, skin adhesion and humidity resistance without having problems of hard structures and being brittle and prone to breakage. Therefore, the base manufactured from the base solution can be demolded smoothly during the stage of production without being liable to break; in the meantime, it can provide sufficient support as well as good softness, flatness, flexibility and skin adhesion during the stage of use, and prolong the storage time of microneedle patches.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A base composition, comprising a first hydroxypropyl methylcellulose, a second hydroxypropyl methylcellulose and a polyvinylpyrrolidone/vinyl acetate copolymer, the viscosity of the first hydroxypropyl methylcellulose being 400 centipoises to 10,000 centipoises, and the viscosity of the second hydroxypropyl methylcellulose being 1 centipoise to 100 centipoises, wherein based on a total weight of the base composition, a total amount of the first hydroxypropyl methylcellulose and the second hydroxypropyl methylcellulose is 0.1 wt % to 3 wt %, a weight ratio of the first hydroxypropyl methylcellulose relative to the second hydroxypropyl methylcellulose is 1:0.1 to 1:1.2, and an amount of the polyvinylpyrrolidone/vinyl acetate copolymer is 0.25 wt % to 2 wt %.

2. The base composition as claimed in claim 1, wherein the total amount of the first hydroxypropyl methylcellulose and the second hydroxypropyl methylcellulose is 0.2 wt % to 2.5 wt %.

3. The base composition as claimed in claim 1, wherein the weight ratio of the first hydroxypropyl methylcellulose relative to the second hydroxypropyl methylcellulose is 1:0.2 to 1:1.

4. The base composition as claimed in claim 1, wherein the viscosity of the first hydroxypropyl methylcellulose is 1,000 centipoises to 8,000 centipoises, and the viscosity of the second hydroxypropyl methylcellulose is 2 centipoises to 50 centipoises.

5. The base composition as claimed in claim 3, wherein the viscosity of the first hydroxypropyl methylcellulose is 1,000 centipoises to 8,000 centipoises, and the viscosity of the second hydroxypropyl methylcellulose is 2 centipoises to 50 centipoises.

6. The base composition as claimed in claim 1, wherein a solid content of the base composition is 0.35 wt % to 60 wt %.

7. The base composition as claimed in claim 2, wherein a solid content of the base composition is 0.35 wt % to 60 wt %.

8. The base composition as claimed in claim 3, wherein a solid content of the base composition is 0.35 wt % to 60 wt %.

9. The base composition as claimed in claim 5, wherein a solid content of the base composition is 0.35 wt % to 60 wt %.

10. The base composition as claimed in claim 1, wherein a viscosity of the base composition is 1 centipoise to 200,000 centipoises.

11. The base composition as claimed in claim 1, wherein the surface tension of the base composition is 25 dyne/cm to 50 dyne/cm.

12. The base composition as claimed in claim 1, wherein the base composition consists of the first hydroxypropyl methylcellulose, the second hydroxypropyl methylcellulose, the polyvinylpyrrolidone/vinyl acetate copolymer and water.

13. A microneedle patch, comprising multiple microneedle structures, each microneedle structure having a base and a needle tip formed on the base, wherein the base is made from the base composition as claimed in claim 1.

* * * * *